United States Patent [19]

Zichis, deceased et al.

[11] 4,228,148

[45] Oct. 14, 1980

[54] HETEROPHIL ANTIBODY DIFFERENTIATION (HAD) TEST

[76] Inventors: Joseph Zichis, deceased, late of Rancho Sante Fe, Calif.; Lillian K. Zichis, executrix, P.O. Box 48, Rancho Sante Fe, Calif. 92067

[21] Appl. No.: 5,497

[22] Filed: Jan. 22, 1979

Related U.S. Application Data

[62] Division of Ser. No. 689,308, May 24, 1976, Pat. No. 4,139,606.

[51] Int. Cl.$^2$ .................... G01N 31/00; G01N 33/16; A61K 35/18
[52] U.S. Cl. ................... 424/12; 23/230 B; 424/85; 424/88; 424/101; 424/103
[58] Field of Search .................. 424/8, 11, 12, 85, 88, 424/101, 103; 23/230 B

[56] References Cited

U.S. PATENT DOCUMENTS

| | | | |
|---|---|---|---|
| 3,426,123 | 2/1969 | Hoff | 424/12 |
| 3,826,821 | 7/1974 | Zichis | 424/13 X |

OTHER PUBLICATIONS

Lee & Davidsohn, Exhibit flyer, 4 pp., Joint Annual Meeting ASCP & CAP, Chicago, Ill., Sep. 22-30, 1967.

*Primary Examiner*—Anna P. Fagelson
*Attorney, Agent, or Firm*—Knobbe, Martens, Olson, Hubbard & Bear

[57] ABSTRACT

Three antigens, termed HA, MN and FN, are prepared for the serological diagnosis of infectious mononucleosis; the HA antigen being used to identify the heterophil antibodies and the FN and MN antigens are used to differentiate them.

1 Claim, No Drawings

HETEROPHIL ANTIBODY DIFFERENTIATION (HAD) TEST

This is a division of Ser. No. 689,308, filed May 24, 1976, now U.S. Pat. No. 4,139,606.

This invention relates to a serological diagnostic test for infectious mononucleosis and to methods for preparing reagents used in that test and the method of performing the test.

For convenience and uniformity, the following designations for the test and the respective antigens have been adopted:

HAD test refers to the heterophil antibody differentiation test described herein using the HA antigen prepared according to the teachings of this specification; HA refers to the heterophil antibody reactive antigen; FN refers to the Forssman antibody neutralizing antigen; and MN refers to the infectious mononucleosis antibody neutralizing antigen.

Infectious mononucleosis is thought to be of a viral etiology; however, it differs from the usual viral diseases in that in its course it produces a particular type of heterophil antibody [1] in the patient's blood. Diagnosis of infectious mononucleosis is complicated, however, by the fact that about 4% of patients carry other classes of heterophil antibodies, such as the Forssman type antibody, serum sickness antibody and horse sensitization antibody [1, 2, 3, 4, 7]. (Bracketed numbers refer to literature citations at the end of the specification.).

In some respects, these antibodies are related and therefore have some similar reactions. But the infectious mononucleosis heterophil antibody and the Forssman antibody, also have dissimilar properties. They react with substance not related to their production and each agglutinates sheep, mule or horse erythrocytes. However, they are also different. The Forssman antibodies are neutralized, according to this invention, by the FN antigen and the infectious mononucleosis antibodies are neutralized by the MN antigen whereas the serum sickness and the horse sensitization antibodies which are encountered rarely may be neutralized by both the FN and MN antigens. These characteristics are utilized in combination with new and highly advantageous antigens for the diagnosis of infectious mononucleosis according to the present invention.

A method, known as the Davidsohn test, [5,6] has been widely used. It is performed by the tube method and, consequently, does not have the advantages and characteristics of the slide diagnosis methods. In the Davidsohn test, the antigen consists of raw washed sheep erythrocytes. The differential part of the test is made with preparation from guinea pig kidneys and beef erythrocytes. It has been used for a long time and has served as a standard for many of the later tests; however, the Davidsohn test has many faults and is unsatisfactory in a number of respects. For example, the preparation of the sheep blood antigen is time-consuming and the resulting antigen lacks stability and uniformity; i.e., variations between individual animals. The differential part of the test is made by absorbing the test serum with preparations of guinea pig kidneys or beef erythrocytes and involves comparative titrations of the absorbed and the unabsorbed serum. It is performed by the tube method and the results are read after several hours of reactivity.

Slide tests have been used for laboratory diagnosis of infectious mononucleosis,[8]. The antigens for such tests are prepared either from sheep or horse erythrocytes, which are treated by various methods. In most cases, these antigens lack stability. Typically, about half way through the dated life time, the avidity of the antigen for the antibody becomes low and the agglutinations which are formed become quite fine. This makes it difficult to read the test reactions and introduces an element of uncertainty into the result.

A principal feature of the present invention is to provide dependable reagents with which a reliable serological diagnostic test may be made for infectious mononucleosis.

One of the features of the invention is that the HA antigen is strongly avid, is highly stable and is highly sensitive. It reacts with a comparatively low titer (1-8) positive infectious mononucleosis serum, producing a heavy, flocculent agglutination, which is easily read and has a long lifetime without loss of avidity, retaining the property of producing a heavy, easily readable flocculent agglutination for a year or longer, as confirmed by data summarized in Table II reported hereinafter.

Another feature of the invention is that the MN and FN antigens are a soluble, stable type and they possess strong neutralizing properties. They are relatively clear and impart very little cloudiness to the test field on the slide, consequently, the test remains easy to read and provides more definitive results.

Another feature of the invention is to provide a diagnostic method whereby the heterophil antibody related to infectious mononucleosis may be identified and differentiated from Forssman type (including serum sickness) antibodies in a single test; thus establishing a diagnosis of the disease in a few minutes time.

Another feature of the invention is to provide uniformity in test reactions during the dated time of the reagents. The antigen of this invention is standardized to give a distinct floccular agglutination with a 1-10 titer positive infectious mononucleosis serum. Through its stability, the same type of reaction is obtained throughout a one year dated time period and for even longer periods, as shown hereinafter in Table II. This makes it easier to read the test and makes the results of the test more dependable.

Another feature of the present invention resides in the composition and utilization of certain special solutions. For convenience, the solutions are designated I-1, S-1, I-2 and S-2, the I and S designations indicating incubation and special solutions. Typical compositions of these solutions are shown in Table I.

TABLE I

| Component | I-1 | I-2 | S-1 | S-2 |
|---|---|---|---|---|
| Water | 2.0 l. | 2.0 l. | 2.0 l. | 2.0 l. |
| KH$_2$PO$_4$ | 13.6 g. | 13.2 g. | 19.0 gl | 13.2 g. |
| K$_2$HPO$_4$ | — | 30.0 g. | — | 30.0 g. |
| NaN$_3$ | 4.0 g. | 4.0 g. | 4.0 g. | 4.0 g. |
| Tris (hydroxymethyl aminomethane) | 8.0 g. | — | 12.0 g. | — |
| Glucose | — | — | 100.0 g. | 100.0 g. |
| (EDTA)K (Potassium ethylene diamine tetraacetic acid) | — | — | — | 6.0 g.* |

*(EDTA)K, or other anti-coagulant, is added optionally for use with whole blood in certain circumstances.

The method of utilization of these solutions and the resulting antigen characteristics are discussed in detail hereinafter. The ratios given above are optimum but not critical and reasonable variation in the ratios and amounts of the individual constituents is comprehended within this invention. In general, ratio variations of from about 0.5:1 to 1:2, based on the above ratios as being 1:1, of individual constituents may be considered generally equivalent but yield and/or quality tends to decrease with departure from the optimum ratios given in Table I.

According to this invention, heterophil antibodies in the patient's serum, plasma or whole blood, are detected by testing the serum, plasma or whole blood with the HA antigen prepared from horse, mule or sheep blood. The infectious mononucleosis antibody is identified by neutralization tests with the MN and FN antigens. The FN antigen neutralizes Forssman type antibodies and the MN antigen neutralizes the infectious mononucleosis antibody. On the slide in which the antibody has been neutralized, the subsequent test with the HA antigen is negative. These tests are performed on a glass slide and are visually read. The entire test requires only a few minutes.

According to this invention, a white-grayish HA antigen for the serological diagnosis of infectious mononucleosis is produced by the incubation of horse, mule or sheep blood in either I-1 or I-2 solution at about pH 7 for from about 3 to 6 days at a temperature of about 36° C.

In a more particular aspect, the invention may be regarded as a white-grayish HA antigen for the serological diagnosis of infectious mononucleosis resulting from incubating horse, mule or sheep blood in either I-1 or I-2 solution at about pH 7 for about 3 to about 6 days at temperature of not more than about 36° C., separating the antigen from blood hemoglobin and proteins, and dispersing the antigen in S-2 solution for storage for a year or more, the antigen being characterized by stability with high avidity for long storage periods of a year or more. The antigen may be prepared from blood which has been previously treated with potassium ethylenediamine tetraacetic acid, or mechanically defibrinated.

The processes of preparing the HA antigen is an important facet of the invention.

In another facet, the invention includes the MN antigen for use in the serological diagnosis of infectious mononucleosis prepared by heating heavily lysed beef erythrocytes in distilled water at about 95° C. for a time of about one-half hour sufficient to extract antigen from said erythrocytes, precipitating the MN antigen from the clear extract of the preceding step with zinc sulphate, and separating the precipitated antigen from the extract supernate.

The process of preparing MN antigen is also a facet of the invention.

In yet another facet, the invention includes the FN antigen for use in serological diagnosis of infectious mononucleosis prepared by suspending ground guinea pig or horse kidney tissue in saline solution; maintaining the suspension prepared to the preceding step at a temperature of from about 2° to about 4° C. to thereby extract antigen into said solution; heating the suspension to about 95° C. and maintaining said temperature for a period of about one-half hour sufficient to extract recoverable quantities of FN antigen into the extract solution; separating the coagulated tissue from the extract solution; adjusting the pH of the extract solution to about pH 7; precipitating the FN antigen with zinc sulphate and mechanically separating the precipitated antigen from the extract solution supernate; and dispersing the antigen in S-2 solution.

The process of preparing the FN antigen is likewise an important facet of the invention.

In one important facet, the invention includes the HAD serological diagnostic test for infectious mononucleosis comprising the steps of mixing on a slide an aliquot of human blood fraction suspected to contain the heterophil antibody characteristic of infectious mononucleosis with a soluble MN antigen which neutralizes without visible agglutination the infectious mononucleosis antibody; mixing on a slide an aliquot of said human blood fraction suspected to contain the heterophil antibody characteristic of infectious mononucleosis with a soluble FN antigen which neutralizes without visible agglutination the Forssman type antibodies but not the infectious mononucleosis antibody; adding to each of the mixtures resulting from the preceding steps HA antigen prepared by the incubation of horse, mule or sheep blood in I-1 or I-2 solution which antigen is agglutinative with both the unneutralized Forssman type and the unneutralized mononucleosis antibodies; and observing the results; in the case of a positive test for infectious mononucleosis, the occurrence of agglutination on the slide having thereon the mixture containing the FN antigen and no agglutination on the slide having thereon the MN antigen.

The HA Antigen

The HA antigen is prepared by incubating the blood of either horse, mule or sheep with an aqueous solution of potassium acid phosphate, Tris and sodium azide at pH approximately 7. The pH may suitably vary from, for example, about 6.8 to about 7.4, and while pH 7 is optimum, the exact pH is not highly critical.

Alternatively, the aqueous incubating solution for horse, mule or sheep comprises basic potassium phosphate, potassium acid phosphate and sodium azide at approximately pH 7.

The blood from which the antigen is prepared may be mechanically defibrinated or treated with an anticoagulant such as one of the salts of EDTA, e.g., potassium ethylenediamine tetraacetic acid (EDTA)K. To obtain uniformity in the erthyrocyte concentration, the whole blood is used and the cell volume is considered to be 40%. Preferably, the solution contains an anticontaminant which prevents the growth of microorganisms which may affect the antigen and, to this extent, acts as a preservative.

No particular concentration of Tris and/or phosphate salts is required but typical concentrations are shown in the specific examples given hereinafter. It will be understood, of course, that the specific concentrations, steps and procedure described hereinafter are exemplary and that considerable variation within the skill of the art may be made without departing from the scope, concept and teaching of the invention.

It is significant that not all systems which may be regarded as buffers are suitable for preparation of the HA antigen. In particular, it is found that the HA antigen cannot be made using an acetate buffer.

The following example is exemplary of a suitable method for preparing the HA antigen from horse, mule or sheep blood.

1. Thoroughly but gently mix 150 ml. of either defibrinated horse, mule or sheep blood.

2. To 2,000 ml. of distilled water add 8 gms. of Tris, 13.6 gms. of potassium acid phosphate and 4 gms. of sodium azide. If necessary, adjust the solution to approximately pH 7 with either Tris or with potassium acid phosphate. This is I-1 solution.

3. Combine the blood of Step No. 1 with the solution of Step No. 2 and mix the suspension gently but thoroughly. This results in a 3% suspension, by volume, of erythrocytes based on the volume of packed erythrocytes.

4. Place the suspension from Step No. 3 in a dry incubator at approximately 36° C. and mix at about 4 hour intervals. Allow the suspension to settle overnight and continue the process from 3 to 6 days, 3 to 5 days being optimum, until a white-grayish sediment forms. Longer incubation can be used but the quality and quantity of antigen is not increased and eventually degrades. In general the shortest incubation times which give satisfactory yield result in superior antigen product. This white-grayish sediment is the HA antigen. The 36° C. temperature is optimum as higher temperatures tend to destroy the antigen and lower temperature extend the reaction time longer than is desirable. Slightly lower temperatures and corresponding lengthened incubation times may be used according to the teachings of this invention but with less satisfactory results.

5. After the antigen forms, from the incubation described in Step No. 4, the antigen is separated from the other blood substances, such as hemoglobin and blood proteins by centrifuging the suspension at about 5,000 rpm for approximately 30 minutes. Three distinct layers form during centrifugation, the HA antigen is a white-grayish layer and is formed as the middle of the three layers. The top and bottom layers are devoid of antigenic activity and are discarded. The HA antigen is further washed with S-1 solution to remove the blood substances. In the process of separation, the antigen packs loosely and overlays the bottom hard-packed layer. The top layer is light and is drawn off with low suction. The top layer must be drawn off with considerable care to avoid loss of the antigen layer. The antigen layer is then separated from the hard-packed layer by washing it off with a syringe. The antigen is then disbursed for a special wash with a special solution. This dispersion is conveniently done by drawing the antigen suspension into the syringe and expressing it two or three times.

6. The antigen is then washed with special solution No. 1, referred to as S-1. S-1 is prepared by adding to 10 liters of distilled water, 500 gms of glucose USP; 60 gms. of Tris; 95 gms. of potassium acid phosphate, and 20 gms of sodium azide. If necessary, the pH is adjusted to 7 with either Tris or acid potassium hydrogen phosphate.

The antigen is washed, one part antigen in twenty parts of S-1, by centrifugation, each time separating the antigen as described in Step No. 5. The antigen is washed until the supernate is clear and colorless. Usually, two washings are sufficient.

7. After the antigen is prepared from either horse, mule or sheep blood and washed in the special solution S-1, it is taken out in special solution No. 2, S-2, which is prepared as follows. To 2 liters of distilled water add 13.2 gms. of potassium acid phosphate, 30 gms. of basic potassium phosphate, 100 gms of glucose (USP) and 4 gms. of sodium azide. If necessary, adjust the solution to pH 7 with either the basic or the acid phosphate salt. The antigen resulting from the 150 ml. of either horse, mule or sheep blood is taken up in 100 ml. of S-2 solution. One of the particularly unique and advantageous characteristics of this invention is the great flexibility permitted as to the form of the sample to be tested. Blood serum is advantageously used. Plasma or whole blood, however, may also be used. It is necessary that whole blood be treated with an anticoagulant, (EDTA)K for example. If a blood sample is to be stored before use, then the anticoagulant is added to the blood before storage. If fresh blood, from a finger or ear lobe puncture for example, is the test sample, then the anticoagulant is advantageously integrated into the antigen reagent solution. This is a particular advantage in pediatric practice and in screening large numbers of patients where serum separation is undesirable, impracticable or prohibitively time consuming or expensive. In the case where the anticoagulant is to be integrated into the antigen reagent, the anticoagulant, (EDTA)K for example, is conveniently formulated into the take-up solution, S-2 solution with added (EDTA)K, in a concentration of about 3.0 mg/cc, being the preferred take-up solution.

The S-1 solution was found to be effective in removing hemoglobin and other blood proteins from the HA antigen without destructing its properties whereas the S-2 solution is effective in preserving the properties of the HA and the other antigens referred to in this patent.

If it is desired to prepare HA antigen from EDTA treated blood, the same procedure is followed from Step No. 1 through Step No. 7.

If it is advantageous, the HA antigen may be prepared with the phosphate system, without Tris. The antigen incubation solution I-2 may be prepared, in an exemplary embodiment, as follows: To 2 liters of distilled water, add 13.2 gms of potassium dihydrogen phosphate, 30 gms. of potassium monohydrogen phosphate, and 4 gms. of sodium azide. The antigen is prepared as described in Step Nos. 1 through 7 except for the substitution of the antigen incubation solution.

Standardization of HA Antigen

The HA antigen, which is prepared from either horse, mule or sheep blood, is standardized as follows:

1. Make serial dilution of the antigen in S-2 solution from one part antigen in one part S-2 solution to one part antigen in 15 parts S-2 solution.

2. Place one drop of each dilution on a one inch square marked on a glass plate.

3. To each such drop add one drop of standard positive infectious mononucleosis serum. Standardized human serum obtained from known cases of the disease and having a titer of 1–160.

4. Mix the reagents on each square with a wooden applicator, going from high to low dilutions.

5. Tilt the plate back and forth in a rotating motion over an indirect light and read the agglutination reaction. The dilution which reacts the fastest, and shows a heavy flocculent agglutination is the titer of the antigen. For use, the HA antigen is then made up in this dilution.

The remarkable stability of the HA antigen prepared as just described, using the S-1 wash procedure and taken up in S-2 solution, is illustrated by the date in Table II.

TABLE II

| Date of Test | Lot No. | Serum Dilution | | | | | |
| --- | --- | --- | --- | --- | --- | --- | --- |
| | | 1:5 | 1:40 | 1:80 | 1:60 | 1:320 | 1:640 |
| Start | 20 | 4 | 4– | 3 | 2 | 2 | +1 |
| Start | 26 | 4 | 4 | 3 | 2 | 2– | 1 |
| Start + 2 mo. | 20 | 4 | 3+ | 3 | 2 | 2 | — |

TABLE II-continued

| Date of Test | Lot No. | Serum Dilution | | | | | |
|---|---|---|---|---|---|---|---|
| | | 1:5 | 1:40 | 1:80 | 1:60 | 1:320 | 1:640 |
| Start + 2 mo. | 26 | 4 | 4 | 3 | 2 | 2 | — |
| Start + 6 mo. | 20 | 4 | 3 | 2 | 2 | 2 | — |
| Start + 6 mo. | 26 | 4 | 4 | 3 | 2 | 2 | — |
| Start + 9 mo. | 20 | 4 | 3— | 2 | 2 | 2 | — |
| Start + 9 mo. | 26 | 4 | 3+ | 3 | 2 | 2 | — |
| Start + 1 yr. | 20 | 4 | 3— | 2 | 2 | 2— | — |
| Start + 1 yr. | 26 | 4 | 3— | 3— | 2— | 2— | — |
| Start + 14 mo. | 20 | 4 | 3 | 2 | 2 | 1+ | — |
| Start + 14 mo. | 26 | 4 | 3 | 2 | 2 | 2— | — |

Two antigens, Lots 20 and 26, were titered, diluted 1:3 in S-2 solution and stored in 10 cc dropper vials at 2°–4° C. The antigens were tested against sera prepared from a known case of infectious mononucleosis having a titer of 1–320 in the dilutions shown in Table II. The respective dilutions were made with S-2 solution and stored in separate 10 cc vials at 2°–4° C.

MN Antigen

The MN antigen is prepared from beef erythrocytes obtained from mechanically defibrinated or (EDTA)K treated beef blood. The blood is diluted one part of blood in one part normal saline, then the cells are separated by centrifugation and washed twice in saline. The packed cells are then diluted one to one in distilled water and homogenized in a Waring blender and then further diluted to a total dilution of one part of cells in four parts of distilled water. The heavily lysed cells are then slowly heated with stirring at intervals of 5 minutes in a double boiler to 95° C. and kept at this temperature for a period long enough to extract the MN antigen, about one-half hour being sufficient. The coagulated cells are broken up with a blender and the extract is separated from the solid by centrifugation or filtration. The clear extract is adjusted to about pH 7 and the MN antigen is separated from the clear extract by precipitation with zinc sulphate and separated by centrifugation. The procedure including the use of zinc sulphate as a precipitating agent is another significant and important feature of the present invention.

A representative method for preparing MN antigen from beef blood is as follows:

1. To 500 ml. of defibrinated beef blood, add 500 ml. of saline.
2. Separate the erythrocytes by centrifugation, and wash once more in saline.
3. Dilute the packed cells 1 to 1 with distilled water, and homogenize with a Waring blender.
4. Further dilute the cell dispersion to a total dilution of one part cells to four parts of distilled water.
5. Heat the dispersion of cells while stirring at 5 minute intervals to 95° C. and hold the dispersion at this temperature for long enough to extract the antigen, typically about thirty minutes.
6. Disperse the coagulated cells, which result from Step No. 5, in a blender and separate the extract from the solids by centrifugation or filtration.
7. Adjust the extract to about pH 7, using, preferably, a potassium phosphate salt.
8. Precipitate the MN antigen by adding 0.25% zinc sulphate to the extract and allow precipitate to form for one hour at room temperature.
9. Separate the precipitated antigen by centrifugation.
10. Harvest the precipitated MN antigen in 100 ml. of S-2 solution.

The MN antigen prepared as described is heat-stable and soluble.

If it is desired to use (EDTA)K treated beef blood, the same procedure is followed as described in Step Nos. 1 through 10.

Standardization of MN Antigen

MN antigen is standardized against a standard positive infectious mononucleosis serum by determining its neutralizing effect against the antibodies of the serum. An exemplary standardization procedure is as follows:

1. Select positive infectious mononucleosis sera which contain titers of 1–800, 1–1200 and 1–1400 with HA antigen.
2. Place one drop of each serum on individual one inch squares marked on a glass plate.
3. To each square add one drop of MN antigen, mix thoroughly with separate wooden applicators and allow to react for five minutes.
4. Add one drop of HA antigen to each dilution. Mix and observe to determine whether or not agglutination occurs.
5. If no agglutination occurs, in all dilutions of the serum, then adjust the MN antigen by diluting with S-2 solution, to a positive neutralization of antibodies in a serum of 1–1200 titer. However, if agglutination occurs in the 1–800 titer serum, then the MN antigen must be adjusted by concentration to neutralize a 1–1200 titer serum.

FN Antigen

The soluble FN antigen is prepared by making a saline extract of guinea pig or horse kidneys, and then isolating the antigen from the extract by precipitating with zinc sulphate. An exemplary method of preparation is as follows:

1. Cut 200 gms. of guinea pig or horse kidneys into small pieces then grind in a Waring blender at full speed for five minutes.
2. Suspend the ground tissue in 2 liters of cooled saline, and add 4 gms. of sodium azide. This results in a 10% tissue suspension and 0.2% sodium azide solution.
3. Store the 10% tissue suspension resulting from Step No. 2 at from about 2° to about 4° C. for about 24 hours to allow extraction.
4. Heat the suspension resulting from Step No. 3 slowly in a double boiler to about 95° C. and hold the heated suspension at this temperature, with stirring, for about 30 minutes, i.e., long enough to extract recoverable amounts of FN antigen.
5. Remove the coagulated tissues, resulting from Step No. 4, by centrifugation or filtration, and discard the sediment. The antigen containing extract is saved and cooled to 25° C.
6. Adjust the volume of the antigen containing extract from Step No. 5 with saline to a volume of 2,000 ml. and adjust to a pH of about 7 with acid or basic potassium phosphate salt.
7. Add 6 gms. (0.3%) of zinc sulphate and allow the antigen to precipitate for about one hour at room temperature.
8. Separate the antigen by centrifugation and harvest it in 100 ml. of S-2 solution.

The FN antigen is standardized by testing it against a standard Forssman heterophil serum. The titer of the serum is determined by testing it with a HA antigen. The FN antigen is then adjusted to neutralize a Forssman serum having a titer of 1–400 or higher.

As described above the HAD serological diagnostic test for infectious mononucleosis depends on the reaction of three antigens specially prepared according to this invention. The HA antigen readily detects both the infectious mononucleosis and the Forssman type heterophil antibodies. The MN antigen neutralizes the infectious mononucleosis antibody. The FN antigen neutralizes Forssman antibodies. Employing these reactive properties of the antigens, it is possible to make an accurate, serological diagnosis of infectious mononucleosis.

The test is performed on a presumptive and differential basis. The specimen is first tested with the HA antigen and, if the results are positive, the heterophil antibodies are identified by the differential method, using the FN and MN antigens.

Presumptive Test

1. Shake the HA antigen thoroughly, and place a drop of it on each of two one inch squares, marked on a glass plate. Then add a drop of the specimen to the first square, and add a drop of saline to the next square. Mix the reagents with separate applicators, and allow them to react for about two minutes.

2. Read the results by slowly rotating the glass plate over an indirect light for about two minutes. The final results should be read about five minutes later.

In a positive presumptive test, agglutination will occur in the first square, but it will not occur in the second square. Such results show the presence of heterophil antibodies, but, to establish a positive diagnosis for infectious mononucleosis, it is necessary to identify the antibody associated with the disease by the differential test with the FN and MN antigens. Any clumping occurring in the second square, indicates that the HA antigen is defective, and should not be used.

HAD Test

1. All the reagents must be shaken thoroughly before they are used in the test.

2. Place a drop of either serum*, plasma, or whole blood on each of three one inch squares marked on a glass plate. 6 * Test sera should be examined and if particles are present, the particles should be removed, by centrifugation or filtration. In case of prozone the test sera or antigen should be diluted.

3. To the first square, add a drop of MN antigen; to the second square, add a drop of FN antigen; to the third square, add a drop of saline; and to each of the fourth, fifth and sixth squares, add two drops of saline.

4. Mix the reagents in the first three squares with separate applicators, and allow them to react for about two minutes.

5. Add a drop of the HA antigen to each of the first four squares, to the fifth square, add a drop of the MN antigen, and to the sixth square, add a drop of the FN antigen. Mix the reagents with separate applicators, and react them for about two minutes.

6. Read the agglutination results by slowly rotating the glass plate over an indirect light for about two minutes. The final results should be read five minutes later.

In a positive test, there will be no agglutination on the first square, but agglutination will occur on the second and third squares. The fourth, fifth and sixth squares are control tests on the angigens. If any clumping appears on any of these squares, the respective antigen is defective and should not be used.

These antigens become defective as a result of freezing, drying (if the vial is not stoppered properly) or insufficient dispersion.

In a negative test, there will be no agglutination in either of the squares (indicating that there are no heterophil antibodies present), or there will be agglutination with the MN and HA antigens, but not the FN antigen. Such reaction shows the presence of the Forssman antibody, which is neutralized by the FN antigen.

Also, neutralization may occur with both the FN and MN antigens, indicating the presence of serum sickness or horse serum sensitization antibodies.

In rare cases, agglutination may occur in the presence of all three antigens. This may happen if both the Forssman and the specific infectious mononucleosis antibodies are present. It may also result if only one of the two antibodies is present, but its titer is higher than the FN or MN antigens are capable of neutralizing. A differential titration of the specimen must be made to resolve these conditions.

If the titer of the positive specimen is desired, it may easily be established by testing serial dilutions of it with the HA antigen.

The character of the agglutination formed in a positive test for infectious mononucleosis with the HA antigen, depends on the type of specimen tested, and on the antibody titer of the patient's blood. Testing either serum or plasma with a high antibody titer, a heavy flocculant agglutination occurs; but if the antibody titer of the specimen is low, then the agglutination is light and dispersed. On the other hand, if whole blood is used for the test, the type of agglutination formed is quite different. It is stringy and resembles a cobweb formation. Likewise, the agglutination varies in intensity with high and low antibody titers of the specimen. With a high antibody titer, the agglutination appears in heavy shreds which tend to clump; whereas, with a low antibody titer, the shreds are light and dispersed.

Eight hundred and twenty five (825) human sera, which tested positive by the Davidsohn presumptive method, were tested on a comparative basis by the present invention, and the Davidsohn differential test. The presumptive titer of the sera varied from 1-7 to 1-896.

By the Davidsohn differential test, 674 of these sera tested positive for infectious mononucleosis, and 151 sera tested negative. When the same sera were tested by the method of this invention, 682 sera tested positive, and 143 sera tested negative for the disease. The results of the tests were consistent, in that, with both methods, the sera reacted similarly.

In the course of these tests, four sera were found to be of the Forssman type.

The reliability of the whole blood method of this invention was evaluated by comparatively testing whole blood and plasma obtained from eighty-six (86) diagnosed cases of infectious mononucleosis. The results of the tests with both the whole blood and the plasma were in total agreement, testing positive for the disease. Also, whole blood and plasma taken from sixty-five (65) healthy persons were likewise tested. Of this number, one person tested positive for the Forssman type antibody, while the other sixty-four (64) specimens tested negative for hererophil antibodies with both the whole blood and the plasma. In addition, whole blood and plasma specimens were obtained from four people who were known to be Forssman antibody positive, and were tested with the antigens of this invention. Both the whole blood and the plasma tested postiive for the Forssman antibody, confirming the presence of the Forssman antibody in these people.

Two hundred of the above sera were selected at random and comparatively tested with the antigens prepared as described in the invention from horse blood, mule blood and sheep blood. The horse blood antigen was found to be most sensitive and to possess the highest avidity with the sheep blood antigen ranking second in sensitivity and avidity and the mule blood ranking third in sensitivity and avidity. All efforts to produce antigen from donkey blood were unsuccessful.

Two hundred sera which tested negative by the sheep washed erythrocyte method were also tested by the method of this invention and were found to test negative.

This invention has been described by exemplary procedures, materials, and techniques to illustrate the best embodiment of the invention presently known to the inventor. Many alterations, modifications and variations may, however, be made which are equivalent to the methods and procedures and materials described in the exemplary embodiment of the specification. Accordingly, it is intended to encompass within the scope of this invention those methods, materials, and procedures and the equivalents thereof which fall within the broad concept of the invention and within the spirit of the scope of the claims which are appended to and part of this specification.

References

1. Paul. J. R. and Bunnel, W. W., Am. J. Med. Sci. 183:90, 1932.
2. Gailey, G. H. and Raffel, S., J. Clin. Investigation, 14:228, 1935.
3. Barrett, A. M., J. Hyg. 41:330, 1941.
4. Hoff, G. and Bauer, S., J. A.M.A., 194:351, 1965.
5. Davidsohn, I., et al, Am. J. Clin. Path., 21:1101, 1951.
6. Davidsohn, I., J. A.M.A., 108:389, 1937.
7. Forssman, J., Biochem. Z., 37:78, 1911.
8. Zichis, U.S. Pat. No. Re. 28,548.

I claim as my invention:

1. The heterophil antibody differentiation test comprising the steps of:

placing at spaced areas on a slide three samples of blood, plasma or serum suspected of containing infectious mononucleosis heterophil antibody;

adding to the first sample an aliquot of infectious mononucleosis antibody neutralizing antigen, MN, composition prepared by heating heavily lysed beef erythrocytes dispersed in water to about 95° C. and maintaining the same at that temperature for about one-half hour, separating the solids from the mixture resulting from the preceding step, adjusting the pH of the supernatant solution to about pH 7 with acid or basic potassium phosphate, adding zinc sulphate to the solution to precipitate the MN antigen, separating the precipitated MN antigen from the supernatant solution and dispersing the antigen in a phosphate buffer solution;

adding to the second sample an aliquote of Forssman antibody neutralizing antigen, FN, composition prepared by storing commminuted guinea pig or horse kidney tissue in saline solution containing $NaN_3$ at from about 2° to 4° C. for about 24 hours, heating the resulting suspension to about 95° C. and maintaining it at that temperature for about one-half hour, separating the solids from the supernatant liquid and cooling the liquid to about 25° C., adjusting the pH of the cooled supernatant liquid to about pH 7 with acid or basic potassium phosphate, precipitating the FN antigen from the solution by the addition of zinc sulphate, separating the precipitated FN antigen from the supernatant solution and dispersing the antigen in a phosphate buffer solution;

adding to each of said samples an aliquot of heterophil antibody reactive antigen, HA, composition resulting from incubating horse, mule or sheep blood in aqueous solution of $KH_2PO_4$, Tris and $NaN_3$ at about pH 7 for about 3 to about 6 days at a temperature of not more than about 36° C., separating the antigen from blood hemoglobin and proteins, and dispersing the antigen in a solution of $KH_2PO_4$, $K_2HPO_4$, $NaN_3$ and glucose; and observing each of said sample mixtures for agglutination, in the case of a positive test for infectious mononucleosis there being no agglutination in the first sample mixture and there being agglutination in the second and third sample mixtures.

* * * * *